US009924712B2

(12) United States Patent
Xu et al.

(10) Patent No.: US 9,924,712 B2
(45) Date of Patent: Mar. 27, 2018

(54) LIQUID CONCENTRATE FORMULATION CONTAINING A PYRIPYROPENE INSECTICIDE II

(71) Applicant: BASF SE, Ludwigshafen (DE)

(72) Inventors: Wen Xu, Cary, NC (US); Matthias Pohlman, Freinsheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/383,756

(22) PCT Filed: Mar. 11, 2013

(86) PCT No.: PCT/EP2013/054826
§ 371 (c)(1),
(2) Date: Sep. 8, 2014

(87) PCT Pub. No.: WO2013/135605
PCT Pub. Date: Sep. 19, 2013

(65) Prior Publication Data
US 2015/0141242 A1 May 21, 2015

Related U.S. Application Data

(60) Provisional application No. 61/609,412, filed on Mar. 12, 2012.

(51) Int. Cl.
| | | |
|---|---|---|
| *A01N 53/00* | (2006.01) | |
| *A01N 25/02* | (2006.01) | |
| *A01N 25/22* | (2006.01) | |
| *A01N 25/30* | (2006.01) | |

(52) U.S. Cl.
CPC ............. *A01N 25/02* (2013.01); *A01N 25/22* (2013.01); *A01N 25/30* (2013.01); *A01N 53/00* (2013.01)

(58) Field of Classification Search
CPC ........ A01N 53/00; A01N 25/02; A01N 25/22; A01N 25/30
See application file for complete search history.

(56) References Cited

U.S. PATENT DOCUMENTS

| | | | |
|---|---|---|---|
| 3,948,636 A | 4/1976 | Marks | |
| 5,089,259 A | 2/1992 | Wessling et al. | |
| 5,807,721 A | 9/1998 | Omura et al. | |
| 6,495,595 B2 | 12/2002 | Moore et al. | |
| 6,521,785 B2 | 2/2003 | Shannon et al. | |
| 6,706,666 B2 | 3/2004 | Hasebe | |
| 7,241,454 B2 | 7/2007 | Warrington et al. | |
| 7,268,259 B1 | 9/2007 | Behler et al. | |
| 7,491,738 B2 * | 2/2009 | Goto | A01N 43/90 514/338 |
| 2004/0106523 A1 * | 6/2004 | Stridde | A01N 25/02 504/362 |
| 2004/0157743 A1 | 8/2004 | Rosenfeldt et al. | |
| 2006/0165748 A1 | 7/2006 | Arimoto | |
| 2008/0096763 A1 | 4/2008 | Dawson et al. | |
| 2008/0300313 A1 * | 12/2008 | Byrne | A01N 25/02 514/611 |
| 2008/0312290 A1 | 12/2008 | Vermeer et al. | |
| 2010/0281584 A1 | 11/2010 | Horikoshi et al. | |
| 2012/0046470 A1 | 2/2012 | Fukuda et al. | |
| 2013/0184153 A1 | 7/2013 | Dieleman et al. | |
| 2013/0190360 A1 * | 7/2013 | Xu | A01N 43/90 514/338 |
| 2014/0142289 A1 | 5/2014 | Anzai et al. | |
| 2014/0371178 A1 | 12/2014 | Horikoshi et al. | |

FOREIGN PATENT DOCUMENTS

| | | |
|---|---|---|
| CA | 2 609 527 | 12/2006 |
| EP | 2 036 437 | 3/2009 |
| EP | 2 107 060 | 10/2009 |
| EP | 2 186 815 | 5/2010 |
| EP | 2 223 599 | 9/2010 |
| EP | 1 889 540 | 11/2011 |
| EP | 2 119 361 | 10/2013 |
| JP | 2993767 | 10/1999 |
| JP | 2002-522400 | 7/2002 |
| JP | 2002-532464 | 10/2002 |
| JP | 2005154344 A * | 6/2005 |
| WO | WO 94/09147 | 4/1994 |
| WO | WO 94/09417 | 4/1994 |
| WO | WO 98/35553 | 8/1998 |
| WO | WO 00/07709 | 2/2000 |
| WO | WO 00/35863 | 6/2000 |
| WO | WO 2004/060065 | 7/2004 |
| WO | WO 2007/117001 | 10/2007 |
| WO | WO 2007/129714 | 11/2007 |
| WO | WO 2008/013336 | 1/2008 |
| WO | WO 2008/108491 | 9/2008 |

(Continued)

OTHER PUBLICATIONS

Office Action dated Sep. 30, 2014 in U.S. Appl. No. 13/822,514.
Office Action dated Oct. 1, 2014 in U.S. Appl. No. 13/822,530.
Final Office Action dated Apr. 2, 2015 in U.S. Appl. No. 13/822,514.
Office Action dated Apr. 20, 2015 in U.S. Appl. No. 13/822,530.
Office Action dated Jul. 13, 2015 in U.S. Appl. No. 14/383,661.
Narayanan, K.S., et al. "Macro and Microemulsion technology and trands", Pesticide Formulation and Adjuvant Technology, Foy, C.L. and Pritchard, D.W., CRC Press, Boca Raton, FL, 1996, p. 148-164.
Sunazuka, Toshiaki, et al., "Synthetic Study of α-Pyrone Meroterpenoids, Pyripyropens", Journal of Society of Synthetic Organic Chemistry, 1998, pp. 478-488, vol. 56, No. 6.

(Continued)

*Primary Examiner* — John Pak
*Assistant Examiner* — Nathan W Schlientz
(74) *Attorney, Agent, or Firm* — Brinks Gilson & Lione

(57) ABSTRACT

The present invention relates to a liquid concentrate formulation comprising a pyripyropene pesticide of the formula I as defined below and an alkoxylated aliphatic alcohol as an adjuvant. Moreover, the invention relates to the use of the formulations for the treatment of plants and seed and to corresponding methods.

20 Claims, No Drawings

(56) References Cited

FOREIGN PATENT DOCUMENTS

| WO | WO 2009/081851 | 7/2009 |
|---|---|---|
| WO | WO 2010010955 | 1/2010 |
| WO | WO 2010131676 | 11/2010 |
| WO | WO 2011/113052 | 9/2011 |
| WO | WO 2011/147952 | 12/2011 |
| WO | WO 2011/147953 | 12/2011 |
| WO | WO 2012/035015 | 3/2012 |
| WO | WO 2012035010 | 3/2012 |
| WO | WO 2013/135604 | 9/2013 |
| WO | WO 2013/135606 | 9/2013 |
| WO | WO 2013/135610 | 9/2013 |

OTHER PUBLICATIONS

Omura, Satoshi, et al., "Pyripyropense, highly potent inhibitors of Acyl-CoA: Cholesterol Acyltransferase produced by *Aspergillus fumigatus*", Journal of Antibiotics, 1993, p. 1168-9, vol. 46, No. 7.

Wang, Hui-Juan, et al., Aflavinines and Other Antiinsectan Metabolites from the Ascostromata of *Eupenicillium crustaceum* and related Species, Applied and Environmental Microbiology, 1995, p. 4429-35, vol. 61, No. 12.

Wang, C.J., et al. "Foliar uptake of pesticides—present status and future challenge", Pesticide Biochemistry and Physiology, 2007, p. 1-8, vol. 87.

International Search Report dated Mar. 28, 2013, prepared in International Application No. PCT/EP2013/054826.

International Preliminary Report on Patentability dated Sep. 16, 2014, prepared in International Application No. PCT/EP2013/054826.

Unknown Author, "Noyaku Seizai Gaido", Japan Plant Protection Association, 1997, pp. 26-31 and 104-112, Pesticide Science Society of Japan, Special Committees on Agricultural Formulation and Application.

Office Action dated Jan. 29, 2016 in U.S. Appl. No. 13/822,530, filed Mar. 12, 2013.

Office Action dated Jan. 20, 2016 in U.S. Appl. No. 13/822,514, filed Mar. 12, 2013.

Final Office Action dated May 17, 2016 in U.S. Appl. No. 13/822,530.

Office Action dated Jan. 5, 2017 in U.S. Appl. No. 14/383,731.

Office Action dated Mar. 14, 2017 from U.S. Appl. No. 14/383,665, filed Sep. 8, 2014.

Office Action dated Sep. 8, 2016 in U.S. Appl. No. 134/383,665.

Office Action dated Jun. 8, 2017 from U.S. Appl. No. 13/822,514, filed Mar. 12, 2013.

U.S. Appl. No. 13/822,530, which is a national stage application in the U.S. of International Application No. PCT/EP2011/065848, filed Sep. 13, 2011. The International Application was published in the English language under International Publication No. WO 2012/035010, and is listed on the enclosed PTO/SB/08.

U.S. Appl. No. 13/822,514, which is a national stage application in the U.S. of International Application No. PCT/EP2011/065855, filed Sep. 13, 2011. The International Application was published in the English language under International Publication No. WO 2012/035015, and is listed on the enclosed PTO/SB/08.

U.S. Appl. No. 14/383,731, which is a national stage application in the U.S. of International Application No. PCT/EP2013/054828, filed Mar. 11, 2013. The International Application was published in the English language under International Publication No. WO 2013/135606, and is listed on the enclosed PTO/SD/08.

U.S. Appl. No. 14/383,661, which is a national stage application in the U.S. of International Application No. PCT/EP2013/054825, filed Mar. 11, 2013. The International Application was published in the English language under International Publication No. WO 2013/135604, and is listed on the enclosed PTO/SB/08.

U.S. Appl. No. 14/383,665, which is a national stage application in the U.S. of International Application No. PCT/EP2013/054836, filed Mar. 11, 2013. The International Application was published in the English language under International Publication No. WO 2013/135610, and is listed on the enclosed PTO/SB/08.

Office Action dated Sep. 7, 2017 from U.S. Appl. No. 14/383,665, filed Sep. 8, 2107.

* cited by examiner

LIQUID CONCENTRATE FORMULATION CONTAINING A PYRIPYROPENE INSECTICIDE II

This application is a National Stage application of International Application No. PCT/EP2013/054826, filed Mar. 11, 2013, which claims the benefit of U.S. Provisional Application No. 61/609,412, filed Mar. 12, 2012, the entire contents of which are hereby incorporated herein by reference.

The present invention relates to a liquid concentrate formulation comprising a pyripyropene pesticide of the formula I as defined below and an alkoxylated aliphatic alcohol as an adjuvant. Moreover, the invention relates to the use of the formulations for the treatment of plants and seed and to corresponding methods.

The pyripyropene derivative of formula I

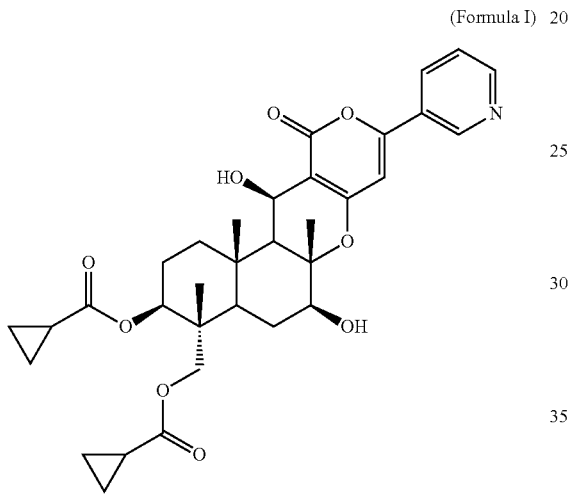

(Formula I)

is known from WO 2009/081851 (compound no. 4) as exhibiting insecticidal activity and being useful for crop protection. In particular, WO 2009/081851 discloses various agrochemical formulations of the pyripyropene derivative I and suitable additives for such formulations.

Agrochemical formulations of pyripyropene derivatives including suitable additives are also disclosed in EP 2 119 361 and EP 1 889 540.

The pyripyropene derivative I may be prepared by the process described in WO 2006/129714 or EP 2 186 815.

One problem associated with agricultural formulations of pyripyropene derivatives, in particular the pyripyropene derivatives of formula I, is that concentrate formulations of these compounds often have only low stability. In particular when trying to provide agricultural formulations of the pyripyropene derivative I in solubilized form one frequently faces the problem that the formulation disintegrates due to settling or agglomeration of active ingredient particles. This is typically caused by pyripyropene derivative I forming solvate complexes with the solvent that is included in the formulation. However, solvents that, owing to their better solubilization of pyripyropene derivative I, may be able to overcome this problem, often have unfavorable toxic profiles rendering them unsuitable for agricultural applications.

In addition, polyalkoxylated alcohols (herein also called alkoxylated alcohols) have been demonstrated to significantly enhance the insecticidal activity of pyripyropene derivative I (see WO 2012/035015) and are therefore highly desirable adjuvants to be included in formulations of the pyripyropene derivative I. However, dependent on the solvent polyalkoxylated alcohols may interfere with the solubilization of the pyripyropene derivative I and they may therefore be incompatible with certain solvents. In fact, the inventors of the present invention found that propylene glycol on the one hand is an excellent solvent for pyripyropene derivative I and also has a favorable toxic profile, while on the other hand, resulting in phase separation if incorporated into pyripyropene derivative I formulations containing a polyalkoxylated alcohol as adjuvant.

Accordingly, it is an object of the present invention to provide stable liquid concentrate formulations of pyripyropene derivative I which besides propylene glycol as solvent also contain an activity enhancing polyalkoxylated alcohol as adjuvant and which have advantageous properties for applications in invertebrate pest control. The formulations should especially provide low toxicity, high insecticidal activity and high stability even after prolonged periods of storage. It is therefore a particular object of the present invention to provide an additive that enables polyalkoxylated alcohols and propylene glycol to be compatible in liquid concentrate formulations of pyripyropene derivative I, so as to prevent phase separation and allow for homogeneous and stable formulations.

Surprisingly, these and other objects are achieved by the liquid concentrate formulations described below.

Accordingly, the present invention provides a liquid concentrate formulation comprising
a) 0.5 to 30 wt %, based on the total weight of the formulation, of the pyripyropene derivative of formula I,
b) 3 to 50 wt %, based on the total weight of the formulation, of propylene glycol,
c) 20 to 85 wt %, based on the total weight of the formulation, of at least one alkoxylated aliphatic alcohol of formula (A)

$$R^a—O—(C_mH_{2m}O)_x—(C_nH_{2n}O)_y—(C_pH_{2p}O)_z—R^b \quad (A)$$

in which
$R^a$ represents $C_8$-$C_{36}$-alkyl, $C_8$-$C_{36}$-alkenyl or a mixture thereof;
$R^b$ represents H or $C_1$-$C_{12}$-alkyl;
m, n, p represent, independently of one another, an integer from 2 to 16;
x, y, z represent, independently of one another, a number from 0 to 50; and
x+y+z corresponds to a value from 2 to 50,
d) 1 to 50 wt %, based on the total weight of the formulation, of at least one $C_2$-$C_4$-alkylene carbonate, and
e) 0.5 to 20 wt %, based on the total weight of the formulation, of at least one non-ionic surfactant S that is different from the alkoxylated aliphatic alcohol A,
wherein the combined amounts of the components a), b), c), d) and e) add up to at least 90 wt % of the total amount of the formulation.

The term wt %, as used herein, has to be understood as % by weight.

The invention also relates to formulations according to the invention which are formulated in the form of a liquid concentrates and to aqueous ready-to-use preparations obtained by diluting such formulations with water.

Further subject matters of the present invention relate to the uses of the formulations according to the invention or ready-to-use preparation derived therefrom for combating or controlling invertebrate pests and for protecting growing plants from attack or infestation by invertebrate pests.

Accordingly, further subject matters are a method for protecting plants from attack or infestation by invertebrate pests, such as insects, acarids or nematodes, which method comprises contacting the plant, or the soil or water in which the plant is growing, with said formulation or said ready-to-use preparation in pesticidally effective amounts; a method for controlling invertebrate pests comprising contacting an invertebrate pest or their food supply, habitat, breeding grounds or their locus with said formulation or said ready-to-use preparation in pesticidally effective amounts; a method for protection of plant propagation material comprising contacting the plant propagation material, preferably seeds, with said formulation or said ready-to-use preparation in pesticidally effective amounts; and finally seed, comprising said composition.

The invention has a number of advantages. Thus, the formulations according to the invention are optically transparent homogeneous formulations which are stable for prolonged storage periods even at extreme temperatures of down to −20° C. and up to 66° C., without loosing their advantageous properties. The formulations of the invention can be easily diluted with water to form stable dilutions in the form of an aqueous suspension or emulsion of the pyripyropene derivative I, without formation of phase separation such as creaming or sedimentation. Apart from that the formulations of the invention provide increased pesticidal activity and low toxicity to the environment.

In the context of the present invention, the terms used generically are defined as follows:

The prefix $C_x$-$C_y$ denotes the number of possible carbon atoms in the particular case.

The term "alkyl" refers to saturated straight-chain, branched or cyclic hydrocarbon radicals having generally from 1 to 36 carbon atoms, e.g. methyl, ethyl, propyl, 1-methylethyl (isopropyl), butyl, 1-methylpropyl (sec-butyl), 2-methylpropyl (isobutyl), 1,1-dimethylethyl (tert-butyl), pentyl, 1-methylbutyl, 2-methylbutyl, 3-methylbutyl, 2,2-dimethylpropyl, 1-ethylpropyl, cyclopentyl, hexyl, 1-methylpentyl, n-heptyl, n-octyl, 2-ethylhexyl, n-nonyl, n-decyl, 1-methylnonyl, 2-propylheptyl, n-dodecyl, 1-methyldodecyl, n-tridecyl, n-tetradecyl, n-pentadecyl, n-hexadecyl, n-heptadecyl, n-octadecyl, n-nonadecyl, n-eicosyl, and the like.

The term "alkenyl" as used herein denotes in each case a singly unsaturated hydrocarbon radical having generally from 1 to 36 carbon atoms, e.g. vinyl, allyl (2-propen-1-yl), 1-propen-1-yl, 2-propen-2-yl, methallyl (2-methylprop-2-en-1-yl), 2-buten-1-yl, 3-buten-1-yl, 2-penten-1-yl, 3-penten-1-yl, 4-penten-1-yl, 1-methylbut-2-enyl, hex-2-enyl, 1-methylpent-2-enyl, hep-2-entyl, oct-4-enyl, 2-ethylhex-2-enyl, non-3-enyl, dec-4-enyl, 1-methylnon-3-enyl, 2-propylhept-3-enyl, dodec-2-enyl, 1-methyldodec-3-enyl, tridec-6-enyl, tetradec-4-enyl, pentade-2-encyl, hexadec-6-enyl, heptadec-8-enyl, octadec-2enyl, nonadec-3-enyl, and the like.

The terms "fatty acid", "fatty alcohol", "fatty amine" and "fatty amide" refer to alkanoic acids, alkanols, alkylamines or alkanoic amides having generally from 6 to 30, in particular from 8 to 22 carbon atoms and wherein the saturated alkyl radical may be linear or branched.

The term "$C_2$-$C_4$-alkylene" refers to saturated, divalent straight-chain or branched hydrocarbon radicals having 2, 3, or 4 carbon atoms, such as, for example, ethane-1,2-diyl, propane-1,3-diyl, propane-1,2-diyl, 2-methylpropane-1,2-diyl, butane-1,4-diyl, butane-1,3-diyl(=1-methylpropane-1, 3-diyl), butane-1,2-diyl and butane-2,3-diyl.

The terms "alkoxylated", "ethoxylated", "polyoxyalkylene" or "polyoxyethylene", respectively, mean that OH-functions have been reacted with ethylene oxide or $C_2$-$C_4$-alkylene oxide to form a oligoalkylene oxide (=polyoxyalkylene) or oligoethylene oxide (=polyoxyethylene) group. The degree of alkoxylation or ethoxylation (number average of alkylene oxide or ethylene oxide repeating units) will usually be in the range from 1 to 50 and in particular from 2 to 40 more preferably from 2 to 30.

The term "aryl" refers to aromatic radicals including carbocyclic aromatic radicals such as, for example, phenyl, naphthyl, anthracenyl, and heteroaromatic radicals having generally 1 or 2 heteroatoms selected from the group consisting of O and N, such as, for example, pyridyl, pyrryl, pyrazinyl, pyrimidinyl, purinyl, indolyl, quinolyl, isoquinolyl, imidazolyl, pyrazolyl, indazolyl, furyl, benzofuryl, isobenzofuryl, morpholinyl, oxazolyl, benzoxazolyl, isoxazolyl and benzisoxazolyl.

The liquid concentrate formulations according to the invention contain propylene glycol typically in an amount of 3 to 50 wt %, based on the total weight of the formulation. Generally, the amount of propylene glycol comprised in the formulations of the invention may vary and depend in each individual case on the amounts of the pyripyropene derivative I, the alkoxylated aliphatic alcohol A, the $C_2$-$C_4$-alkylene carbonate, the non-ionic surfactant S and optional further ingredients, and also their properties. The weight ratio of propylene glycol to the amount of the pyripyropene derivative I is usually in the range from 0.2:1 to 40:1, preferably from 0.5:1 to 30:1, in particular from 1:1 to 20:1, and specifically from 2:1 to 10:1. Based on the total weight of the formulations, the proportion of propylene glycol is preferably from 10 to 40% by weight and in particular from 15 to 35% by weight.

The formulations according to the invention comprise at least one alkoxylated aliphatic alcohol of the formula (A), hereinafter also termed as alkoxylate A,

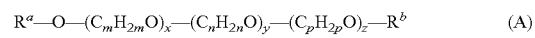

$$R^a\text{—O—}(C_mH_{2m}O)_x\text{—}(C_nH_{2n}O)_y\text{—}(C_pH_{2p}O)_z\text{—}R^b \qquad (A)$$

in which
$R^a$ represents $C_8$-$C_{36}$-alkyl, $C_8$-$C_{36}$-alkenyl or a mixture thereof, preferably $C_{10}$-$C_{32}$-alkyl, $C_{10}$-$C_{32}$-alkenyl, or a mixture thereof, more preferably $C_{14}$-$C_{26}$-alkyl, $C_{14}$-$C_{26}$-alkenyl, or a mixture thereof, in particular $C_{15}$-$C_{20}$-alkyl, $C_{15}$-$C_{20}$-alkenyl, or a mixture thereof;
$R^b$ represents H or $C_1$-$C_{12}$-alkyl, in particular H or $C_1$-$C_4$-alkyl, preferably H or methyl, especially H;
m, n, p represent, independently of one another, an integer from 2 to 16, preferably an integer from 2 to 5, more preferably an integer 2 or 3 (i.e. all of m, n, p are either 2 or 3, or one of m, n, p is 2 and the remaining two are both 3, or one of m, n, p is 3 and remaining two are both 2), specifically one of m, n, p is 2 and the remaining two are both 3 or one of m, n, p is 3 and the remaining two are both 2;
x, y, z represent, independently of one another, a number from 0 to 50, preferably a number from 0 to 30, more preferably from 0 to 20; and
x+y+z corresponds to a value from 2 to 50, preferably from 5 to 50, more preferably from 10 to 30 and in particular from 12 to 20.

The term "alkoxylated" in this context means that the OH moiety of the aliphatic alcohol has been replaced by a polyoxyalkylene or polyalkylene oxide moiety. Polyoxyalkylene, in terms of the present invention, is an aliphatic polyether radical which is build from alkylene oxide repeating units A-O, where A is alkandiyl, in particular $C_2$-$C_5$-alkandiyl.

Polyoxyalkylene, in terms of the present invention, is preferably a poly-$C_2$-$C_5$-alkylene oxide moiety, more preferably a poly-$C_2$-$C_4$-alkylene oxide moiety, especially a poly-$C_2$-$C_3$-alkylene oxide moiety, e.g. a polyethylene oxide moiety, a polypropylene oxide moiety, a poly(ethylene oxide-co-propylene oxide) moiety, a poly(ethylene oxide-co-butylene oxide) moiety or a poly(ethylene oxide-co-pentylene oxide) moiety. The number of alkylene oxide repeating units in the polyoxyalkylene radical is generally from 1 to 100 or from 2 to 100, preferably from 5 to 40, more preferably from 10 to 30 and in particular from 12 to 20.

The variable $R^a$ of the at least one alkoxylate A may be linear or branched, preferably it is linear. $R^a$ may be saturated or unsaturated, preferably it is saturated. $R^a$ may be substituted or unsubstituted, preferably it is unsubstituted. Preferably, $R^a$ represents linear $C_8$-$C_{36}$-alkyl, $C_8$-$C_{36}$-alkenyl, or a mixture thereof. More preferably, $R^a$ represents linear $C_{14}$-$C_{36}$-alkyl, $C_{14}$-$C_{36}$-alkenyl, or a mixture thereof, in particular linear $C_{14}$-$C_{26}$-alkyl, $C_{14}$-$C_{26}$-alkenyl, or mixture thereof. Even more preferably, $R^a$ represents a linear $C_{14}$-$C_{22}$-alkyl, or a mixture thereof. Especially preferred, $R^a$ represents a linear $C_{16}$-$C_{20}$-alkyl, or a mixture thereof.

$R^b$ represents preferably H or methyl, in particular H.

Preferably, m, n, p represent, independently of one another, an integer from 2 to 5, more preferably an integer 2 or 3, specifically one of m, n, p is 2 and the remaining two are both 3 or one of m, n, p is 3 and the remaining two are both 2.

Preferably, x, y, z represent, independently of one another, a number from 0 to 30, more preferably from 0 to 20. Preferably, the sum x+y+z corresponds to a value from 5 to 40, more preferably from 10 to 30, more preferably from 8 to 25, and in particular from 12 to 20.

According to a particular embodiment, alcohol alkoxylates of the formula (A) are used in which m=2 and the value of x is greater than zero. This relates to alcohol alkoxylates of the EO type to which belong especially alcohol ethoxylates (m=2; x>zero; y and z=zero) and alcohol alkoxylates with an EO block bonded to the alcohol portion that include further alkylene oxide moieties (m=2; x>zero; y and/or z>zero). As regards to the latter compounds, mention may also be made of EO-PO block alkoxylates (m=2; x>zero; y>zero; n=3; z=0), EO-PeO block alkoxylates (m=2; x>zero; y>zero; n=5; z=0) and EO-PO-EO block alkoxylates (m, p=2; x, z>zero; y>zero; n=3). In particular preferred are EO-PO block alkoxylates (m=2; x>zero; y>zero; n=3; z=0).

Here and in the following EO represents $CH_2CH_2O$, PO represents $CH(CH_3)CH_2O$ or $CH_2CH(CH_3)O$, BuO represents $CH(C_2H_5)CH_2O$, $C(CH_3)_2CH_2O$, $CH_2C(CH_3)_2O$, $CH(CH_3)CH(CH_3)O$ or $CH_2CH(C_2H_5)O$ and PeO represents ($C_5H_{10}O$).

In this context preference is given to EO-PO block alkoxylates in which the ratio of EO to PO (x to y) is 10:1 to 1:15, preferably 1:1 to 1:12 and in particular 1:2 to 1:8, with the degree of ethoxylation (value of x) being generally 1 to 20, preferably 2 to 15 and in particular 2 to 10 and the degree of propoxylation (value of y) being generally 1 to 30, preferably 4 to 20 and in particular 8 to 16. The overall degree of alkoxylation, i.e. the sum of EO and PO units, is generally 2 to 50, preferably 4 to 30 and in particular 6 to 20.

In this context preference is furthermore given to EO-PeO block alkoxylates in which the ratio of EO to PeO (x to y) is 2:1 to 25:1 and in particular 4:1 to 15:1, with the degree of ethoxylation (value of x) being generally 1 to 50, preferably 4 to 25 and in particular 6 to 15 and the degree of pentoxylation (value of y) being generally 0.5 to 20, preferably 0.5 to 4 and in particular 0.5 to 2. The overall degree of alkoxylation, i.e. the sum of EO and PeO units, is generally 1.5 to 70, preferably 4.5 to 29 and in particular 6.5 to 17.

According to a further particular embodiment, alcohol alkoxylates of the formula (A) are used in which n=2, the values of x and y are both greater than zero and z=0. This relates to alcohol alkoxylates of the EO type in which the EO block is terminally bonded. These include especially PO-EO block alkoxylates (n=2; x>zero; y>zero; m=3; z=0) and PeO-EO block alkoxylates (n=2; x>zero; y>zero; m=5; z=0).

In this context preference is given to PO-EO block alkoxylates in which the ratio of PO to EO (x to y) is 1:10 to 15:1, preferably 1:1 to 12:1 and in particular 2:1 to 8:1, with the degree of ethoxylation (value of y) being generally 1 to 20, preferably 2 to 15 and in particular 2 to 10, and the degree of propoxylation (value of x) being generally 0.5 to 30, preferably 4 to 20 and in particular 6 to 16. The overall degree of alkoxylation, i.e. the sum of EO and PO units, is generally 1.5 to 50, preferably 2.5 to 30 and in particular 8 to 20.

In this context preference is also given to PeO-EO block alkoxylates in which the ratio of PeO to EO (x to y) is 1:50 to 1:3 and in particular 1:25 to 1:5, with the degree of pentoxylation (value of x) being generally 0.5 to 20, preferably 0.5 to 4 and in particular 0.5 to 2 and the degree of ethoxylation (value of y) being generally 3 to 50, preferably 4 to 25 and in particular 5 to 15. The overall degree of alkoxylation, i.e. the sum of EO and PeO units, is generally 3.5 to 70, preferably 4.5 to 45 and in particular 5.5 to 17.

In an especially preferred embodiment the alkoxylate is selected from alkoxylated alcohols of the formula (A), in which
$R^a$ represents linear $C_{12}$-$C_{22}$-alkyl, especially linear $C_{10}$-$C_{20}$ alkyl or a mixture thereof;
$R^b$ represents H or $C_1$-$C_4$-alkyl, preferably H or methyl, in particular H;
m, n, p represent, independently of one another, an integer from 2 to 5, preferably 2 or 3;
x, y, z represent, independently of one another, a number from 0 to 50; and
x+y+z corresponds to a value from 5 to 50, preferably from 8 to 25.

The wetting power by immersion of the alkoxylate is usually at least 120 seconds, preferably at least 180 s, especially at least 220 s. The wetting power is usually analyzed according to DIN 1772 at room temperature at 1 g/L in 2 g/l sodium carbonate.

The surface tension of the alkoxylate is usually at least 30 mN/m, preferably at least 31 mN/m, and in particular at least 32 mN/m. Furtheron, the surface tension is preferably from 30 to 40 mN/m, and in particular from 30 to 35 mN/m. The surface tension may be analyzed according to DIN 14370 at room temperature at 1 g/L.

Preferably, the alkoxylate has a wetting power by immersion of at least 120 s and a surface tension of at least 30 mN/m. More preferably, the alkoxylate has a wetting power by immersion of at least 180 s and a surface tension from 30 to 40 mN/m.

Alkoxylates are known and may be prepared by known methods, such as WO 98/35553, WO 00/35278 or EP 0 681 865. Many alkoxylates are commercially available, for example Atplus® 242, Atplus® 245, Atplus® MBA 1303 from Croda, Plurafac® LF types from BASF SE, Agnique® BP 24-24, Agnique® BP 24-36, Agnique® BP 24-45, Agnique® BP 24-54, Agnique® BP24-52R from Cognis.

The liquid concentrate formulations according to the invention comprise the at least one alkoxylate A typically in an amount of 20 to 85 wt %, based on the total weight of the formulation. Generally, the amount of alkoxylate A comprised in the formulations of the invention depends in each individual case on the amounts of the pyripyropene derivative I, propylene glycol, the $C_2$-$C_4$-alkylene carbonate, the non-ionic surfactant S and optional further ingredients, and also their properties. The weight ratio of alkoxylate A to the amount of the pyripyropene derivative I is usually in the range from 1:1 to 50:1, preferably from 2:1 to 40:1, in particular from 3:1 to 30:1, and specifically from 4:1 to 20:1. Based on the total weight of the formulations, the proportion of alkoxylate A is preferably from 30 to 80% by weight and in particular from 35 to 75% by weight.

The formulations according to the invention comprise at least one $C_2$-$C_4$-alkylene carbonate.

$C_2$-$C_4$-Alkylene carbonates that are suitable for the inventive formulations include e.g. ethylene carbonate (1,3-dioxolan-2-one), propylene carbonate (4-methyl-1,3-dioxolan-2-one) and 1,2-butylene carbonate (4-ethyl-1,3-dioxolan-2-one), with preference given to propylene carbonate.

According to a preferred embodiment of the invention the at least one $C_2$-$C_4$-alkylene carbonate is propylene carbonate.

The liquid concentrate formulations according to the invention contain the at least one $C_2$-$C_4$-alkylene carbonate typically in an amount of 1 to 50 wt %, based on the total weight of the formulation. Generally, the amount of $C_2$-$C_4$-alkylene carbonate comprised in the formulations of the invention depends in each individual case on the amounts of the pyripyropene derivative I, propylene glycol, alkoxylate A, the non-ionic surfactant S and optional further ingredients, and also their properties. The weight ratio of $C_2$-$C_4$-alkylene carbonate to the amount of the alkoxylate A is usually in the range from 0.005:1 to 10:1, preferably from 0.01:1 to 5:1, in particular from 0.02:1 to 1.5:1, and specifically from 0.04:1 to 1:1. Based on the total weight of the formulations, the proportion of $C_2$-$C_4$-alkylene carbonate is preferably from 1.5 to 40% by weight and in particular from 2 to 35% by weight.

The formulations according to the invention contain at least one non-ionic surfactant S that is different from the alkoxylated aliphatic alcohol A.

The term surfactant refers to surface-active substances, which are also referred to as emulsifiers or detergents. The optional non-ionic surfactant may assist is stabilizing the formulations of the invention, for example by helping to solubilize the pyripyropene derivative I and optional further active compounds and stabilizing aqueous dilutions of the formulations. The skilled worker is familiar with suitable non-ionic surfactants for formulating agrochemical formulations, for example through McCutcheon, Detergents and Emulsifiers, Int. Ed., Ridgewood, N.Y. The non-ionic surfactants may be polymeric or nonpolymeric surfactants. Preferably, the predominant portion, in particular at least 90% and specifically all of the non-ionic surfactant is selected from the group of the nonpolymeric surfactants, which are also referred to as emulsifiers. Usually, nonpolymeric surfactants (emulsifiers) have an average molecular weight of less than 9000 Daltons, in particular from 150 to 6000 Daltons and preferably from 200 to 3000 Daltons.

Non-ionic surfactants that are suitable as surfactants S in the formulation of the invention include in particular:

oligo-$C_2$-$C_3$-alkylene oxide aryl ethers and oligo-$C_2$-$C_4$-alkylene oxide $C_1$-$C_{22}$-alkylaryl ethers, such as, for example, oligo-$C_2$-$C_3$-alkylene oxide $C_1$-$C_{16}$-alkylbenzene ethers, in particular ethoxylates of the $C_1$-$C_{22}$-alkylphenols such as, for example, the ethoxylate of nonylphenol, decylphenol, isodecylphenol, dodecylphenol or isotridecylphenol;

oligo-$C_2$-$C_3$-alkylene oxide mono-, di- or tristyrylphenyl ethers, in particular ethoxylates of the mono-, di- and tristyrylphenols, and their condensates with formaldehyde and their esters, such as, for example, the acetates; $C_6$-$C_{22}$-alkylglucosides and $C_6$-$C_{22}$-alkyloligoglucosides;

ethoxylates of the $C_6$-$C_{22}$-alkylglucosides and ethoxylates of the $C_6$-$C_{22}$-alkyloligoglucosides;

ethoxylates of the fatty acids and ethoxylates of the hydroxyl fatty acids;

partial esters of polyols with $C_6$-$C_{22}$-alkanoic acids, in particular mono- and diesters of glycerol and mono-, di- and triesters of sorbitan, such as, for example, glycerol monostearate, sorbitan monododecanoate, sorbitan dioleate and sorbitan tristearate;

ethoxylates of the partial esters of polyols with $C_6$-$C_{22}$-alkanoic acids, in particular ethoxylates of the mono- and diesters of glycerol and ethoxylates of the mono-, di- and triesters of sorbitan, such as, for example, ethoxylates of glycerol monostearate, ethoxylates of sorbitan monooleate, ethoxylates of sorbitan monostearate and ethoxylates of sorbitan tristearate;

ethoxylates of vegetable oils or animal fats, such as, for example, corn oil ethoxylate, castor oil ethoxylate, tall oil ethoxylate;

acetylene glycols such as, for example, 2,4,7,9-tetramethyl-4,7-dihydroxy-5-decyne; and ethoxylates of fatty amines or of fatty acid diethanolamides.

In this context, the terms oligo-$C_2$-$C_3$-alkylene oxide ether and oligo-$C_2$-$C_3$-alkylene oxide refer to oligoether radicals which are derived from $C_2$-$C_3$-alkylene oxides such as ethylene oxide and propylene oxide (=1-methyloxirane). The term ethoxylate refers to oligoether radicals which are derived from ethylene oxide. The number of repeat units in the oligoether radicals is generally between 2 and 120, frequently between 4 and 80, and in particular between 5 and 60.

Among the aforementioned non-ionic surfactants, the following are preferred as surfactants S:

oligo-$C_2$-$C_3$-alkylene oxide $C_1$-$C_{16}$-alkylbenzene ethers, in particular ethoxylated $C_1$-$C_{16}$-alkylphenols;

oligo-$C_2$-$C_3$-alkylene oxide mono-, di- or tristyrylphenyl ethers, in particular ethoxylated di- or tristyrylphenols;

partial esters of glycerol or sorbitan with fatty acids; and ethoxylates of monofatty acid esters of sorbitan, and also mixtures of the non-ionic surfactants mentioned hereinabove.

Non-ionic surfactants S which are particularly preferred in the context of the present invention include monofatty acid esters of sorbitan, ethoxylated sorbitan monofatty acid esters and di- or tristyrylphenol ethoxylates, and mixtures of these.

Preferably, the non-ionic surfactant S is at least one oligo-$C_2$-$C_3$-alkylene oxide di- or tristyrylphenyl ether, in particular at least one di- or tristyrylphenol ethoxylate, especially at least one tristyrylphenol ethoxylate.

Non-ionic non-ionic surfactants S are known in the art and are commercially available. Thus, tristyrylphenol ethoxylates are available e.g. under the trade names Soprophor® BSU (Rhodia), Emulsogen® TS 160 (Clariant) and Emulsogen® TS 200 (Clariant).

The liquid concentrate formulations according to the invention comprise the at least one non-ionic surfactant S typically in an amount of 0.5 to 20 wt %, based on the total weight of the formulation. The weight ratio of non-ionic surfactant S to the amount of the pyripyropene derivative I is usually in the range from 0.05:1 to 20:1, preferably from 0.1:1 to 10:1, in particular from 0.2:1 to 4:1, and specifically from 0.3:1 to 2:1. Based on the total weight of the formulations, the proportion of non-ionic surfactant S is preferably from 1 to 10% by weight and in particular from 2 to 7% by weight.

The liquid concentrate formulations according to the invention generally comprise the pyripyropene derivative of formula I in a concentration of from 0.5 to 30 wt %, frequently from 1 to 20 wt %, in particular from 1 to 10 wt %, specifically from 2 to 10 wt % or from 3 to 7 wt %, based on the total weight of the formulation. In the case of one or more further active compounds, such as for crop protection, in addition to the pyripyropene derivative I, the total concentration of active compounds is generally in the range from 1 to 40 wt %, frequently in the range from 1 to 30 wt % and in particular in the range from 2 to 25 wt % or in the range from 2.5 to 15 wt %, based on the total weight of the formulation.

The liquid concentrate formulations according to the invention may also comprise water. As regards the total weight of the undiluted formulation, the amount of water is, as a rule, in the range of up to 10 wt %, preferably up 7 wt % and in particular up to 6 wt %. It is obvious that the amount of water and the amounts of the remaining constituents total 100% by weight.

According to one embodiment the liquid concentrate formulations of the invention comprise 0.5 to 10 wt %, preferably 1 to 7 wt % and in particular 2 to 6 wt % of water.

According to a preferred embodiment the liquid concentrate formulations of the invention do not comprise water or virtually do not comprise water, i.e. less than 2 wt %, preferably less than 1 wt % and in particular less than 0.5 wt % of water.

In a preferred embodiment of the invention, the formulations according to the invention comprise:
a) from 1 to 10 wt %, in particular from 2 to 10 wt % or 3 to 7 wt %, based on the total weight of the formulation, of pyripyropene derivative of the formula I;
b) from 10 to 40 wt %, in particular from 15 to 35 wt %, based on the total weight of the formulation, of propylene glycol,
c) from 30 to 80 wt %, in particular from 35 to 75 wt %, based on the total weight of the formulation, of at least one alkoxylated aliphatic alcohol of the formula (A);
d) from 1.5 to 40 wt %, in particular from 2 to 35 wt %, based on the total weight of the formulation, of at least one $C_2$-$C_4$-alkylene carbonate, and
e) from 1 to 10 wt %, in particular from 2 to 7 wt %, based on the total weight of the formulation, of at least one non-ionic surfactant S, wherein the combined amounts of the components a), b), c), d) and e) add up to at least 90 wt %, in particular to at least 95 wt % and specifically to at least 98 wt %, of the total amount of the formulation.

In preferred formulation according to the invention the at least one alkoxylate is the sole adjuvant used for enhancing the insecticidal activity of pyripyropene derivative I. However, the alkoxylate A may also be combined with an additional different adjuvant. In the latter case, the inventive formulations comprise at least one alkoxylate A and at least one adjuvant different therefrom, the total amount of adjuvant is generally at least 20 wt %, e.g. form 20 to 90 wt %, preferably at least 35 wt %, and in particular from 35 to 80 wt %, based on the total weight of the formulation.

In addition to the pyripyropene derivative of formula I the formulations according to the invention may comprise further active compounds for crop protection for increasing the activity and/or for broadening the application spectrum, such as additional insecticides, e.g. insecticidal compounds having similar or complementary activity in respect of pyripyropene derivative I, or compounds with completely different biological activity, such as herbicides, fungicides and plant growth regulators. However, in general pyripyropene derivative of formula I is the only active compound or constitutes at least 80 wt %, preferably at least 90 wt % of the active compounds comprised in the formulation.

The inventive composition may also comprise auxiliaries which are customary in agrochemical compositions. The auxiliaries used depend on the particular application form and active substance, respectively. Examples for suitable auxiliaries are organic and inorganic thickeners, bactericides, anti-freezing agents, anti-foaming agents, and, if appropriate, colorants and tackifiers or binders (e.g. for seed treatment formulations).

Examples for thickeners (i.e. compounds that impart a modified flowability to formulations, i.e. high viscosity under static conditions and low viscosity during agitation) are polysaccharides and organic and anorganic clays such as Xanthan gum (Kelzan®, CP Kelco, U.S.A.), Rhodopol® 23 (Rhodia, France), Veegum® (R.T. Vanderbilt, U.S.A.) or Attaclay® (Engelhard Corp., N.J., USA). Bactericides may be added for preservation and stabilization of the formulation. Examples for suitable bactericides are those based on dichlorophene and benzylalcohol hemi formal (Proxel® from ICI or Acticide® RS from Thor Chemie and Kathon® MK from Rohm & Haas) and isothiazolinone derivatives such as alkylisothiazolinones and benzisothiazolinones (Acticide® MBS from Thor Chemie). Examples for suitable anti-freezing agents are ethylene glycol, propylene glycol, urea and glycerin. Examples for anti-foaming agents are silicone emulsions (such as e.g. Silikon® SRE, Wacker, Germany or Rhodorsil®, Rhodia, France), long chain alcohols, fatty acids, salts of fatty acids, fluoroorganic compounds and mixtures thereof. Suitable colorants are pigments of low water solubility and water-soluble dyes. Examples to be mentioned and the designations rhodamin B, C. I. pigment red 112, C. I. solvent red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108. Examples for tackifiers or binders are polyvinylpyrrolidons, polyvinylacetates, polyvinyl alcohols and cellulose ethers (Tylose®, Shin-Etsu, Japan).

The customary auxiliaries mentioned above can be added during the preparation of the formulations according to the invention and thus may optionally be contained within the inventive formulations. Alternatively, it is also possible to add these auxiliaries during or after dilution with water to the ready-to-use aqueous formulation, which are described with more detail below.

In general, the liquid concentrate formulation of the invention can be prepared by simply mixing the constituents until an apparently homogeneous liquid has formed. The order in which the constituents are added is usually of minor importance. For example, the constituents may be put into a container and the mixture thus obtained is homogenized, for example by stirring, until a homogeneous liquid has formed. However, it is often advantageous to initially mix together the propylene glycol, the alkoxylate A, the $C_2$-$C_4$-alkylene carbonate, the surfactant S and water, if applicable, and agitate until apparent homogeneity is reached, then to add the pyripyropene derivative I and possibly further active compounds and agitate until all active compounds are apparently completely dissolved. Optional further constituents, such as auxiliaries, can either be intermixed with the thus obtained formulation or added at an earlier stage of the preparation process. The temperature during mixing and the further mixing conditions are of minor importance. Usually, mixing of the constituents is carried out at temperatures of from 10° C. to 50° C., in particular from 10° C. to 40° C. or at ambient temperature.

The invention also relates to aqueous ready-to-use preparations obtained by diluting the formulation of the invention with at least 5 parts of water, preferably at least 10 parts of water, in particular at least 20 parts of water and more preferably at least 50 parts of water, e.g. from 10 to 10,000, in particular from 20 to 1,000 and more preferably from 50 to 250 parts of water per one part of the liquid formulation (all parts are given in parts by weight).

Dilution will be usually achieved by pouring the liquid concentrate formulation of the invention into water. Usually, dilution is achieved with agitation, e.g. with stirring, to ensure a rapid mixing of the concentrate in water. However, agitation is generally not necessary. Though the temperature of mixing is not critical, mixing is usually performed at temperatures ranging from 0 to 50° C., in particular from 10 to 30° C. or at ambient temperature.

The water used for mixing is usually tap water. However the water may already contain water soluble compounds which are used in plant protection, e.g. nutrificants, fertilizers or water soluble pesticides.

The formulations of the invention can be applied in a conventional manner, e.g. in diluted form as an aqueous ready-to-use preparation described above. The inventive aqueous ready-to-use preparations can be applied by spraying, in particular spraying of the leaves. Application can be carried out using spraying techniques known to the person skilled in the art, for example using water as carrier and amounts of spray liquor of about 100 to 1000 liters per hectare, for example from 300 to 400 liters per hectare.

The present invention further relates to a method for controlling insects, arachnids or nematodes comprising contacting an insect, acarid or nematode or their food supply, habitat, breeding grounds or their locus with an inventive formulation or preparation in pesticidally effective amounts.

The inventive composition exhibits outstanding action against animal pests (e.g. insects, acarids or nematodes) from the following orders:

Insects from the order of the lepidopterans (Lepidoptera), for example *Agrotis ipsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Pieris rapae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis*;

beetles (Coleoptera), for example *Agrilus sinuatus, Agriotes lineatus, Agriotes obscurus, Amphimallus solstitialis, Anisandrus dispar, Anthonomus grandis, Anthonomus pomorum, Aphthona euphoridae, Athous haemorrhoidalis, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Cetonia aurata, Ceuthorrhynchus assimilis, Ceuthorrhynchus napi, Chaetocnema tibialis, Conoderus vespertinus, Crioceris asparagi, Ctenicera* ssp., *Diabrotica longicornis, Diabrotica semipunctata, Diabrotica 12-punctata Diabrotica speciosa, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Otiorrhynchus sulcatus, Otiorrhynchus ovatus, Phaedon cochleariae, Phyllobius pyri, Phyllotreta chrysocephala, Phyllophaga* sp., *Phyllopertha horticola, Phyllotreta nemorum, Phyllotreta striolata, Popillia japonica, Sitona lineatus* and *Sitophilus granaria*; flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Ceratitis capitata, Chrysomya bezziana, Chrysomya hominivorax, Chrysomya macellaria, Chrysops discalis, Chrysops silacea, Chrysops atlanticus, Cochliomyia hominivorax, Contarinia sorghicola Cordylobia anthropophaga, Culicoides furens, Culex pipiens, Culex nigripalpus, Culex quinquefasciatus, Culex tarsalis, Culiseta inornata, Culiseta melanura, Dacus cucurbitae, Dacus oleae, Dasineura brassicae, Delia antique, Delia coarctata, Delia platura, Delia radicum, Dermatobia hominis, Fannia canicularis, Geomyza Tripunctata, Gasterophilus intestinalis, Glossina morsitans, Glossina palpalis, Glossina fuscipes, Glossina tachinoides, Haematobia irritans, Haplodiplosis equestris, Hippelates* spp., *Hylemyia platura, Hypoderma lineata, Leptoconops torrens, Liriomyza sativae, Liriomyza trifolii, Lucilia caprina, Lucilia cuprina, Lucilia sericata, Lycoria pectoralis, Mansonia titillanus, Mayetiola destructor, Musca autumnalis, Musca domestica, Muscina stabulans, Oestrus ovis, Opomyza florum, Oscinella frit, Pegomya hysocyami, Phorbia antiqua, Phorbia brassicae, Phorbia coarctata, Phlebotomus argentipes, Psorophora columbiae, Psila rosae, Psorophora discolor, Prosimulium mixtum, Rhagoletis*

*cerasi, Rhagoletis pomonella, Sarcophaga haemorrhoidalis, Sarcophaga* spp., *Simulium vittatum, Stomoxys calcitrans, Tabanus bovinus, Tabanus atratus, Tabanus lineola,* and *Tabanus similis, Tipula oleracea,* and *Tipula paludosa;* thrips (Thysanoptera), e.g. *Dichromothrips corbetti, Dichromothrips* ssp., *Frankliniella fusca, Frankliniella occidentalis, Frankliniella tritici, Scirtothrips citri, Thrips oryzae, Thrips palmi* and *Thrips tabaci,* termites (Isoptera), e.g. *Calotermes flavicollis, Leucotermes flavipes, Heterotermes aureus, Reticulitermes flavipes, Reticulitermes virginicus, Reticulitermes lucifugus, Reticulitermes santonensis, Reticulitermes grassei, Termes natalensis,* and *Coptotermes formosanus;* cockroaches (*Blattaria*-Blattodea), e.g. *Blattella germanica, Blattella asahinae, Periplaneta americana, Periplaneta japonica, Periplaneta brunnea, Periplaneta fuligginosa, Periplaneta australasiae,* and *Blatta orientalis;* bugs, aphids, leafhoppers, whiteflies, scale insects, cicadas (Hemiptera), e.g. *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis, Thyanta perditor, Acyrthosiphon onobrychis, Adelges laricis, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Bemisia argentifolii, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzus persicae, Myzus ascalonicus, Myzus cerasi, Myzus varians, Nasonovia ribis-nigri, Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Trialeurodes vaporariorum, Toxoptera aurantii*and *Viteus vitifolii, Cimex lectularius, Cimex hemipterus, Reduvius senilis, Triatoma* spp., and *Arilus critatus;* ants, bees, wasps, sawflies (Hymenoptera), e.g. *Athalia rosae, Atta cephalotes, Atta capiguara, Atta cephalotes, Atta laevigata, Atta robusta, Atta sexdens, Atta texana, Crematogaster* spp., *Hoplocampa minuta, Hoplocampa testudinea, Lasius niger, Monomorium pharaonis, Solenopsis geminata, Solenopsis invicta, Solenopsis richteri, Solenopsis xyloni, Pogonomyrmex barbatus, Pogonomyrmex californicus, Pheidole megacephala, Dasymutilla occidentalis, Bombus* spp., *Vespula squamosa, Paravespula vulgaris, Paravespula pennsylvanica, Paravespula germanica, Dolichovespula maculata, Vespa crabro, Polistes rubiginosa, Camponotus floridanus,* and *Linepithema humile;* crickets, grasshoppers, locusts (Orthoptera), e.g. *Acheta domestica, Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Schistocerca americana, Schistocerca gregaria, Dociostaurus maroccanus, Tachycines asynamorus, Oedaleus senegalensis, Zonozerus variegatus, Hieroglyphus daganensis, Kraussaria angulifera, Calliptamus italicus, Chortoicetes terminifera,* and *Locustana pardalina;* arachnoidea, such as arachnids (Acarina), e.g. of the families Argasidae, Ixodidae and Sarcoptidae, such as *Amblyomma americanum, Amblyomma variegatum, Ambryomma maculatum, Argas persicus, Boophilus annulatus, Boophilus decoloratus, Boophilus microplus, Dermacentor silvarum, Dermacentor andersoni, Dermacentor variabilis, Hyalomma truncatum, Ixodes ricinus, Ixodes rubicundus, Ixodes scapularis, Ixodes holocyclus, Ixodes pacificus, Ornithodorus moubata, Ornithodorus hermsi, Ornithodorus turicata, Ornithonyssus bacoti, Otobius megnini, Dermanyssus gallinae, Psoroptes ovis, Rhipicephalus sanguineus, Rhipicephalus appendiculatus, Rhipicephalus evertsi, Sarcoptes scabiei,* and *Eriophyidae* spp. such as *Aculus schlechtendali, Phyllocoptrata oleivora* and *Eriophyes sheldoni;* Tarsonemidae spp. such as *Phytonemus pallidus* and *Polyphagotarsonemus latus;* Tenuipalpidae spp. such as *Brevipalpus phoenicis;* Tetranychidae spp. such as *Tetranychus cinnabarinus, Tetranychus kanzawai, Tetranychus pacificus, Tetranychus telarius* and *Tetranychus urticae, Panonychus ulmi, Panonychus citri,* and *Oligonychus pratensis;* Araneida, e.g. *Latrodectus mactans,* and *Loxosceles reclusa;* fleas (Siphonaptera), e.g. *Ctenocephalides felis, Ctenocephalides canis, Xenopsylla cheopis, Pulex irritans, Tunga penetrans,* and *Nosopsyllus fasciatus,* silverfish, firebrat (Thysanura), e.g. *Lepisma saccharina* and *Thermobia domestica,* centipedes (Chilopoda), e.g. *Scutigera coleoptrata,* millipedes (Diplopoda), e.g. *Narceus* spp., earwigs (Dermaptera), e.g. *forficula auricularia,* lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus.*

Collembola (springtails), e.g. *Onychiurus* ssp.

The formulations and preparations of the present invention are also suitable for controlling nematodes: plant parasitic nematodes such as root knot nematodes, *Meloidogyne hapla, Meloidogyne incognita, Meloidogyne javanica,* and other *Meloidogyne* species; cyst-forming nematodes, *Globodera rostochiensis* and other *Globodera* species; *Heterodera avenae, Heterodera glycines, Heterodera schachtii, Heterodera trifolii,* and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, Criconema species, Criconemella species, Criconemoides species, Mesocriconema species; Stem and bulb nematodes, *Ditylenchus destructor, Ditylenchus dipsaci* and other *Ditylenchus* species; Awl nematodes, Dolichodorus species; Spiral nematodes, *Heliocotylenchus multicinctus* and other *Helicotylenchus* species; Sheath and sheathoid nematodes, Hemicycliophora species and Hemicriconemoides species; Hirshmanniella species; Lance nematodes, *Hoploaimus* species; false rootknot nematodes, Nacobbus species; Needle nematodes, *Longidorus elongatus* and other *Longidorus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus* and other *Rotylenchus* species; Scutellonema species; Stubby root nematodes, *Trichodorus primitivus* and other *Trichodorus* species, *Paratrichodorus* species; Stunt nematodes, *Tylenchorhynchus claytoni*, *Tylenchorhynchus dubius* and other *Tylenchorhynchus* species; Citrus nematodes, *Tylenchulus* species; Dagger nematodes, *Xiphinema* species; and other plant parasitic nematode species.

The formulations and preparations according to the invention can be applied to any and all developmental stages of pests, such as egg, larva, pupa, and adult. The pests may be controlled by contacting the target pest, its food supply, habitat, breeding ground or its locus with a pesticidally effective amount of the inventive formulations and preparations. "Locus" means a plant, plant propagation material (preferably seed), soil, area, material or environment in which a pest is growing or may grow.

In general, "pesticidally effective amount" means the amount of the inventive formulations and preparations needed to achieve an observable effect on growth, including the effects of necrosis, death, retardation, prevention, and removal, destruction, or otherwise diminishing the occurrence and activity of the animal pest. The pesticidally effective amount can vary for the various formulations and preparations used in the invention. A pesticidally effective amount of the formulations and preparations will also vary according to the prevailing conditions such as desired pesticidal effect and duration, weather, target species, locus, mode of application, and the like.

The inventive formulations and preparations are employed by treating the animal pest or the plants, plant propagation materials (preferably seeds), materials or soil to be protected from pesticidal attack with a pesticidally effective amount of the active compounds. The application can be carried out both before and after the infection of the materials, plants or plant propagation materials (preferably seeds) by the pests.

Preferably, the inventive formulations and preparations are employed by treating the animal pests or the plants or soil to be protected from pesticidal attack via foliar application with a pesticidally effective amount of the active compounds. In addition, the application can be carried out both before and after the infection of the plants by the pests.

In the method of combating animal pests (insects, acarids or nematodes) the application rates of the formulations and preparations according to the invention depend on the intensity of the infestation by pests, on the development phase of the plants, on the climatic conditions at the application site, on the application method, on whether pyripyropene derivative I is used solely or in combination with further active compounds and on the desired effect. In general, the application rate is in the range of from 0.1 g/ha to 10000 g/ha, preferably 1 g/ha to 5000 g/ha, more preferably from 20 to 1000 g/ha, most preferably from 10 to 750 g/ha, in particular from 20 to 500 g/ha of total active compound.

In the context of the present invention, the term plant refers to an entire plant, a part of the plant or the propagation material of the plant.

Plants and as well as the propagation material of said plants, which can be treated with the inventive formulations and preparations include all genetically modified plants or transgenic plants, e.g. crops which tolerate the action of herbicides or fungicides or insecticides owing to breeding, including genetic engineering methods, or plants which have modified characteristics in comparison with existing plants, which can be generated for example by traditional breeding methods and/or the generation of mutants, or by recombinant procedures.

For example, formulations and preparations according to the present invention can be applied (as seed treatment, spray treatment, in furrow or by any other means) also to plants which have been modified by breeding, mutagenesis or genetic engineering including but not limiting to agricultural biotech products on the market or in development (cf. http://www.bio.org/speeches/pubs/er/agri_products.asp). Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-transitional modification of protein(s), oligo- or polypeptides e.g. by glycosylation or polymer additions such as prenylated, acetylated or farnesylated moieties or PEG moieties.

Plants that have been modified by breeding, mutagenesis or genetic engineering, e.g. have been rendered tolerant to applications of specific classes of herbicides, such as hydroxyphenylpyruvate dioxygenase (HPPD) inhibitors; acetolactate synthase (ALS) inhibitors, such as sulfonyl ureas (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e.g. U.S. Pat. No. 6,222,100, WO 01/82685, WO 00/026390, WO 97/41218, WO 98/002526, WO 98/02527, WO 04/106529, WO 05/20673, WO 03/014357, WO 03/13225, WO 03/14356, WO 04/16073); enolpyruvylshikimate-3-phosphate synthase (EPSPS) inhibitors, such as glyphosate (see e.g. WO 92/00377); glutamine synthetase (GS) inhibitors, such as glufosinate (see e.g. EP-A 242 236, EP-A 242 246) or oxynil herbicides (see e.g. U.S. Pat. No. 5,559,024) as a result of conventional methods of breeding or genetic engineering. Several cultivated plants have been rendered tolerant to herbicides by conventional methods of breeding (mutagenesis), e.g. Clearfield® summer rape (Canola, BASF SE, Germany) being tolerant to imidazolinones, e.g. imazamox. Genetic engineering methods have been used to render cultivated plants such as soybean, cotton, corn, beets and rape, tolerant to herbicides such as glyphosate and glufosinate, some of which are commercially available under the trade names RoundupReady® (glyphosate-tolerant, Monsanto, U.S.A.) and LibertyLink® (glufosinate-tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as δ-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, e.g. *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxy-steroid oxidase, ecdysteroid-IDP-glycosyl-transferase, cholesterol oxidases, ecdysone inhibitors or HMG- CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e.g. WO 02/015701). Further examples of such toxins or genetically modified plants capable of synthesizing such toxins are disclosed, e.g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e.g. in the publications mentioned above. These insecticidal proteins contained in the genetically modified plants impart to the plants producing these proteins tolerance to harmful pests from all taxonomic groups of athropods, especially to beetles (Coeloptera), two-winged insects (Diptera), and moths (Lepidoptera) and to nematodes (Nematoda). Genetically modified plants capable to synthesize one or more insecticidal proteins are, e.g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e.g. Agrisure® CB) and Bt176 from Syngenta Seeds SAS, France, (corn cultivars producing the Cry1Ab toxin and PAT enzyme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e.g. EP-A 392 225), plant disease resistance genes (e.g. potato cultivars, which express resistance genes acting against *Phytophthora infestans* derived from the Mexican wild potato *Solanum bulbocastanum*) or T4-lysozym (e.g. potato cultivars capable of synthesizing these proteins with increased resistance against bacteria such as *Erwinia amylvora*). The methods for producing such genetically modified plants are generally known to the person skilled in the art and are described, e.g. in the publications mentioned above.

Furthermore, plants are also covered that are by the use of recombinant DNA techniques capable to synthesize one or more proteins to increase the productivity (e.g. bio mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e.g. oil crops that produce health-promoting long-chain omega-3 fatty acids or unsaturated omega-9 fatty acids (e.g. Nexera® rape, DOW Agro Sciences, Canada).

Furthermore, plants are also covered that contain by the use of recombinant DNA techniques a modified amount of substances of content or new substances of content, specifically to improve raw material production, e.g. potatoes that produce increased amounts of amylopectin (e.g. Amflora® potato, BASF SE, Germany).

The inventive formulations and preparations are effective through both contact (via soil, glass, wall, bed net, carpet, plant parts or animal parts), and ingestion (bait, or plant part) and through trophallaxis and transfer.

Preferred application methods are into water bodies, via soil, cracks and crevices, pastures, manure piles, sewers, into water, on floor, wall, or by perimeter spray application and bait.

Methods to control infectious diseases transmitted by non-phytopathogenic insects (e.g. malaria, dengue and yellow fever, lymphatic filariasis, and leishmaniasis) with the inventive formulations and their respective preparations or compositions also comprise treating surfaces of huts and houses, air spraying and impregnation of curtains, tents, clothing items, bed nets, tsetse-fly trap or the like. Insecticidal compositions for application to fibers, fabric, knitgoods, non-wovens, netting material or foils and tarpaulins preferably comprise a composition including an inventive formulation, optionally a repellent and at least one binder.

The inventive formulations and preparations can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities).

In the case of soil treatment or of application to the pests dwelling place or nest, the quantity of active compound ranges from 0.0001 to 500 g per 100 m$^2$, preferably from 0.001 to 20 g per 100 m$^2$.

Customary application rates in the protection of materials are, for example, from 0.01 g to 1000 g of active compound per m$^2$ treated material, desirably from 0.1 g to 50 g per m$^2$.

The invention further relates to methods for protection of plant propagation material, termed herein also methods for seed treatment, which methods comprise contacting the plant propagation material with a formulation or preparation of the invention or a composition derived therefrom in pesticidally effective amounts. The methods for seed treatment comprise all suitable methods known to the person skilled in the art for treating seed, such as, for example, seed dressing, seed coating, seed soaking, seed film coating, seed multilayer coating, seed encrusting, seed dripping, seed dusting and seed pelleting.

The formulations and preparations of the invention can be used as is for seed treatment. Alternatively, the inventive formulations and preparations can be converted into compositions for seed treatment using methods known to skilled person, e.g. by adding auxiliaries such as colorants, tackifiers or binders.

In a first embodiment of seed treatment according to the invention, the seed, i.e. the plant product capable of propagation, intended for sowing, is treated with an inventive formulation or preparation, or a composition derived therefrom. Here, the term seed comprises seeds and plant parts capable of propagation of any type, including seeds, seed grains, parts of seeds, seedlings, seedlings' roots, saplings, shoots, fruits, tubers, cereal grains, cuttings and the like, in particular grains and seeds.

Alternatively, the seed may also be treated with the inventive formulation or preparation, or a composition derived therefrom, during sowing. In a further embodiment of seed treatment or soil treatment according to the invention, the furrows are treated with the inventive formulation or preparation, or a composition derived therefrom, either before or after sowing of the seed.

In a preferred embodiment of the invention, the inventive formulations or preparations are used for the protection of seeds, seedlings' roots or shoots, preferably seeds.

The seeds which have been treated in accordance with the invention are distinguished by advantageous properties in comparison with conventionally treated seeds and therefore also form part of the subject matter of the present application. The seeds treated this way comprise the inventive formulation generally in an amount of from 0.1 g to 10 kg per 100 kg of seed, preferably 0.1 g to 1 kg per 100 kg of seed.

The following examples further illustrate the present invention:

EXAMPLES

Starting Materials:
Insecticide A: pyripyropene derivative of the formula I.
Adjuvant A: alkoxylated fatty alcohol, liquid at room temperature, wetting power by immersion: >300 s (according to DIN 1772 at 1 g/L in 2 g/l sodium carbonate at 23° C.), water content: 5-10 wt %, surface tension: ca. 32 mN/m (according to DIN 14370 at 1 g/L at 23° C.)—Plurafac® LF 1300 (BASF).
Alkylene carbonate A: propylene carbonate—Jeffsol® AG-1555 (Huntsman).
Surfactant A: tristyrylphenol ethoxylate, ethoxylated with 16 moles of ethylene oxide, HLB value of 12.6-Soprophor® BSU (Rhodia).

The HLB (hydrophilic lipophilic balance) value referred to herein is the HLB value according to Griffin (W. C. Griffin, J. Soc. Cosmet. Chem. 1, 311 (1950); 5, 249 (1954)—see also H. Mollet et al. "Formulation Technology", 1$^{st}$ ed. Wiley-VCH Verlags GmbH, Weinheim 2001, pages 70-73 and references cited therein).

Example 1

Two solutions of pyripyropene derivative I in Alkylene carbonate A having concentrations of 10 wt % and 20 wt %, respectively, were prepared by slowly adding the corresponding amounts of pyripyropene derivative I to well agitated volumes of Alkylene carbonate A. In both cases it took about 1 hour for complete dissolution of pyripyropene derivative I. After the agitation had been continued for additional approximately 2 hours the clear solutions started to turn cloudy, indicating the precipitation of propylene carbonate solvate crystals of pyripyropene derivative I. Microscopical analysis confirmed that the precipitation was indeed crystalline.

Formulation Examples

Examples 2 to 5 and Comparative Example

The Formulation Examples 2 to 5 according to the invention and the Comparative Formulation Example are listed in Table 1. Table 1 shows the ingredients and their amounts used for preparing the respective formulations. The preparations were carried out at room temperature as follows:

The Adjuvant A, propylene glycol, the Surfactant A, and Alkylene carbonate A, if applicable, were initially charged into a container and mixed with stirring until a homogeneous mixture was obtained. Then Insecticide A was added to the mixture and stirring was continued until the Insecticide A was completely dissolved.

II. Stability Tests of the Formulations

The storage stabilities of the prepared formulations were examined by keeping samples of each formulation example for 7 days either at room temperature (22° C.), at a low temperature (−20° C.) or at a high temperature (65° C.). In addition, the samples of Formulation Examples 2 to 6 to be kept at 22° C., prior to the 7 day storage, had been seeded with propylene carbonate solvate crystals of pyripyropene derivative I prepared in Example 1. After the 7 day period the appearances of the samples were monitored. A clear and homogeneous liquid is indicative for a stable formulation, whereas a cloudy, turbid or milky liquid and in particular a liquid showing phase separation or precipitation are indicative for an instable formulation. The results of these stability tests are shown in Table 2 below.

TABLE 1

Formulation examples (the numeric values are proportions in wt %)

| | Example | | | | |
|---|---|---|---|---|---|
| | Comparative | 2 | 3 | 4 | 5 |
| Insecticide A | 5 | 5 | 4.9 | 4.76 | 4.9 |
| propylene glycol | 50 | 19 | 19.1 | 31.24 | 18 |
| Adjuvant A | 40 | 40 | 64 | 40 | 70.6 |
| Alkylene carbonate A | — | 31 | 7 | 19 | 4 |
| Surfactant A | 5 | 5 | 5 | 5 | 2.5 |
| total | 100 | 100 | 100 | 100 | 100 |
| Appearances of completed formulation | th* | ch* | ch* | ch* | ch* |

*abbreviations: th = turbid and inhomogeneous, ch = clear and homogeneous

TABLE 2

Storage stabilities

| | Appearances after storage for 7 days at: | | |
|---|---|---|---|
| Example | 22° C. | −20° C. | 65° C. |
| Comparative | ps | ps | ps |
| 2 | ch | ch | ch |
| 3 | ch | ch | ch |
| 4 | ch | ch | ch |
| 5 | ch | ch | ch |

*abbreviations: ps = phase separation, ch = clear and homogeneous

The results of the stability test demonstrate that the inventive formulations stay stabile for prolonged storage periods not only at room temperature but also at very low and very high temperatures (−20° C. and 65° C.), whereas the comparative formulation which does not include an adjuvant according to the invention, had already dissociated into two phases after the same time period at all three temperatures.

We claim:

1. A liquid concentrate formulation, which comprises
   a) 1 to 10 wt %, based on the total weight of the formulation, of a compound of formula I;

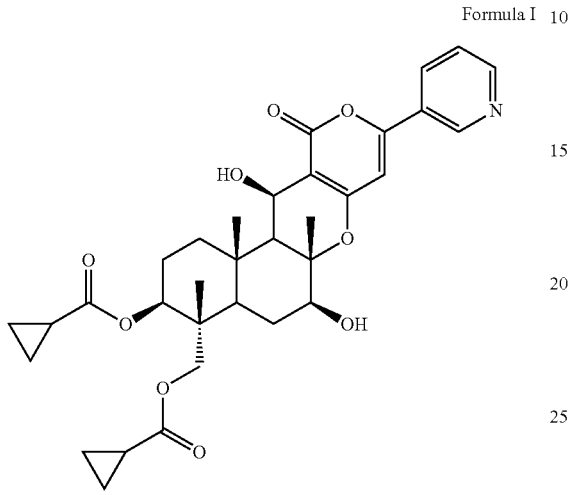

Formula I b) 10 to 40 wt %, based on the total weight of the formulation, of propylene glycol,
c) 30 to 80 wt %, based on the total weight of the formulation, of at least one alkoxylated aliphatic alcohol of formula (A)

$$R^a\text{—}O\text{—}(C_mH_{2m}O)_x\text{—}(C_nH_{2n}O)_y\text{—}(C_pH_{2p}O)_z\text{—}R^b \quad (A)$$

in which
$R^a$ represents a linear $C_{14}$-$C_{36}$-alkyl, or $C_{14}$-$C_{36}$-alkenyl;
$R^b$ represents H or $C_1$-$C_{12}$-alkyl;
m, n and p represent, independently of one another, an integer from 2 to 16;
x, y and z represent, independently of one another, a number from 0 to 50; and
x+y+z corresponds to a value from 2 to 50,
d) 1.5 to 40 wt %, based on the total weight of the formulation, of at least one $C_2$-$C_4$-alkylene carbonate, and
e) 1 to 10 wt %, based on the total weight of the formulation, of at least one non-ionic surfactant S that is different from the alkoxylated aliphatic alcohol of formula (A), wherein the non-ionic surfactant S is at least one oligo-$C_2$-$C_3$-alkylene oxide di- or tristyrylphenyl ether,
wherein the combined amounts of the components a), b), c), d) and e) add up to at least 90 wt % of the total amount of the formulation wherein the weight ratio of component b) to a) is from 2:1 to 10:1; the weight ratio of component c) to a) is from 4:1 to 20:1; the weight ratio of component d) to c) is from 0.04:1 to 1:1; and the weight ratio of component e) to a) is from 0.3:1 to 2:1.

2. The formulation according to claim 1 comprising the non-ionic surfactant S in an amount from 2 to 7 wt %, based on the total weight of the formulation.

3. The formulation according to claim 1, wherein the variables m, n and p in formula (A) represent, independently of one another, an integer from 2 to 5.

4. The formulation according to claim 1, wherein the sum x+y+z of the variables x, y and z in formula (A) corresponds to a value from 5 to 50.

5. The formulation according to claim 1, wherein the $C_2$-$C_4$-alkylene carbonate is propylene carbonate.

6. The formulation according to claim 1, which comprises
   a) 2 to 10 wt %, based on the total weight of the formulation, of the compound of formula I,
   b) 15 to 35 wt %, based on the total weight of the formulation, of propylene glycol,
   c) 35 to 75 wt %, based on the total weight of the formulation, of at least one alkoxylated aliphatic alcohol of the formula (A),
   d) 2 to 35 wt %, based on the total weight of the formulation, of at least one $C_2$-$C_4$-alkylene carbonate, and
   e) 2 to 7 wt %, based on the total weight of the formulation, of at least one non-ionic surfactant S.

7. The formulation according to claim 1, which is formulated in the form of a water-soluble, liquid concentrate.

8. An aqueous ready-to-use preparation obtained by diluting the formulation according claim 1 with water.

9. A method for protecting plants from attack or infestation by invertebrate pests comprising contacting the plant, or the soil or water in which the plant is growing, with a formulation according to claim 1 in pesticidally effective amounts.

10. The method of claim 9, wherein the formulation comprises the non-ionic surfactant S in an amount from 2 to 7 wt %, based on the total weight of the formulation.

11. The method of claim 9, wherein the variables m, n and p in formula (A) represent, independently of one another, an integer from 2 to 5.

12. The method of claim 9, wherein the sum x+y+z of the variables x, y and z in formula (A) corresponds to a value from 5 to 50.

13. The method of claim 9, wherein the $C_2$-$C_4$-alkylene carbonate is propylene carbonate.

14. A method for controlling invertebrate pests comprising contacting an invertebrate pest or their food supply, habitat, breeding grounds or their locus with a formulation according to claim 1 in pesticidally effective amounts.

15. The method of claim 14, wherein the formulation comprises the non-ionic surfactant S in an amount from 2 to 7 wt %, based on the total weight of the formulation.

16. The method of claim 14, wherein the variables m, n and p in formula (A) represent, independently of one another, an integer from 2 to 5.

17. The method of claim 14, wherein the sum x+y+z of the variables x, y and z in formula (A) corresponds to a value from 5 to 50.

18. The method of claim 14, wherein the $C_2$-$C_4$-alkylene carbonate is propylene carbonate.

19. A method for protection of plant propagation material against invertebrate pests comprising contacting the plant propagation material with a formulation according to claim 1 in pesticidally effective amounts.

20. Seed treated with the formulation according to claim 1.

* * * * *